(12) United States Patent
Mateju et al.

(10) Patent No.: US 9,784,425 B2
(45) Date of Patent: Oct. 10, 2017

(54) SIGNAL LAMP

(71) Applicant: Varroc Lighting Systems, s.r.o., Senov u Noveho Jicina (CZ)

(72) Inventors: Tomas Mateju, Bartosovice na Morave (CZ); Tomas Gloss, Vitkov (CZ); Jakub Hruska, Markvartovice (CZ)

(73) Assignee: Varroc Lighting Systems, s.r.o. (CZ)

(*) Notice: Subject to any disclaimer, the term of this patent is extended or adjusted under 35 U.S.C. 154(b) by 0 days.

(21) Appl. No.: 14/990,525

(22) Filed: Jan. 7, 2016

(65) Prior Publication Data

US 2016/0195234 A1    Jul. 7, 2016

(30) Foreign Application Priority Data

Jan. 7, 2015    (CZ) .......................... 2015-2

(51) Int. Cl.
| | | |
|---|---|---|
| *F21S 8/10* | (2006.01) | |
| *A61N 1/04* | (2006.01) | |
| *A61N 1/32* | (2006.01) | |
| *A61N 1/36* | (2006.01) | |

(52) U.S. Cl.
CPC .......... *F21S 48/225* (2013.01); *A61N 1/0468* (2013.01); *A61N 1/32* (2013.01); *A61N 1/36014* (2013.01); *F21S 48/2281* (2013.01); *F21S 48/215* (2013.01); *F21S 48/2262* (2013.01); *F21S 48/2268* (2013.01)

(58) Field of Classification Search
CPC ... B60Q 1/0011; F21S 48/2268; F21S 48/225; F21S 48/2225
See application file for complete search history.

(56) References Cited

U.S. PATENT DOCUMENTS 5,984,497 A      11/1999  Foerstner et al.
2005/0111235 A1*  5/2005  Suzuki ................ B60Q 1/2696
                                                362/555
(Continued)

FOREIGN PATENT DOCUMENTS

| CZ | 20120257 A3 | 10/2013 |
|---|---|---|
| DE | 19652159 A1 | 6/1998 |
| DE | 19831002 A1 | 4/2000 |

(Continued)

OTHER PUBLICATIONS

Search Report from Corresponding Czech Application No. PV 2015-2, Dated Sep. 23, 2015 (3 pages).

*Primary Examiner* — Karabi Guharay
(74) *Attorney, Agent, or Firm* — Hovey Williams LLP

(57) ABSTRACT

A signal lamp comprises at least one light source arranged at the entry of a longitudinal light guide oriented with its longitudinal axis (γ) in the direction (s) of light exit from the lamp, and at least a portion of the light from the light source passes into a transversal light guide oriented with its longitudinal axis (α, β) transversally to longitudinal axis (γ). Transversal light guide is fitted on a part of its casing with an exit surface for light to exit from the lamp. Longitudinal light guide is fitted with at least two reflective surfaces that do not overlap when viewed in the direction of longitudinal axis (γ), and that are inclined towards axis (γ) to reflect light beams to at least two transversal light guides having their entries against the reflective surfaces, and their exit surfaces at a distance from each other in direction (s).

5 Claims, 3 Drawing Sheets

(56) References Cited

U.S. PATENT DOCUMENTS

Figure 1:
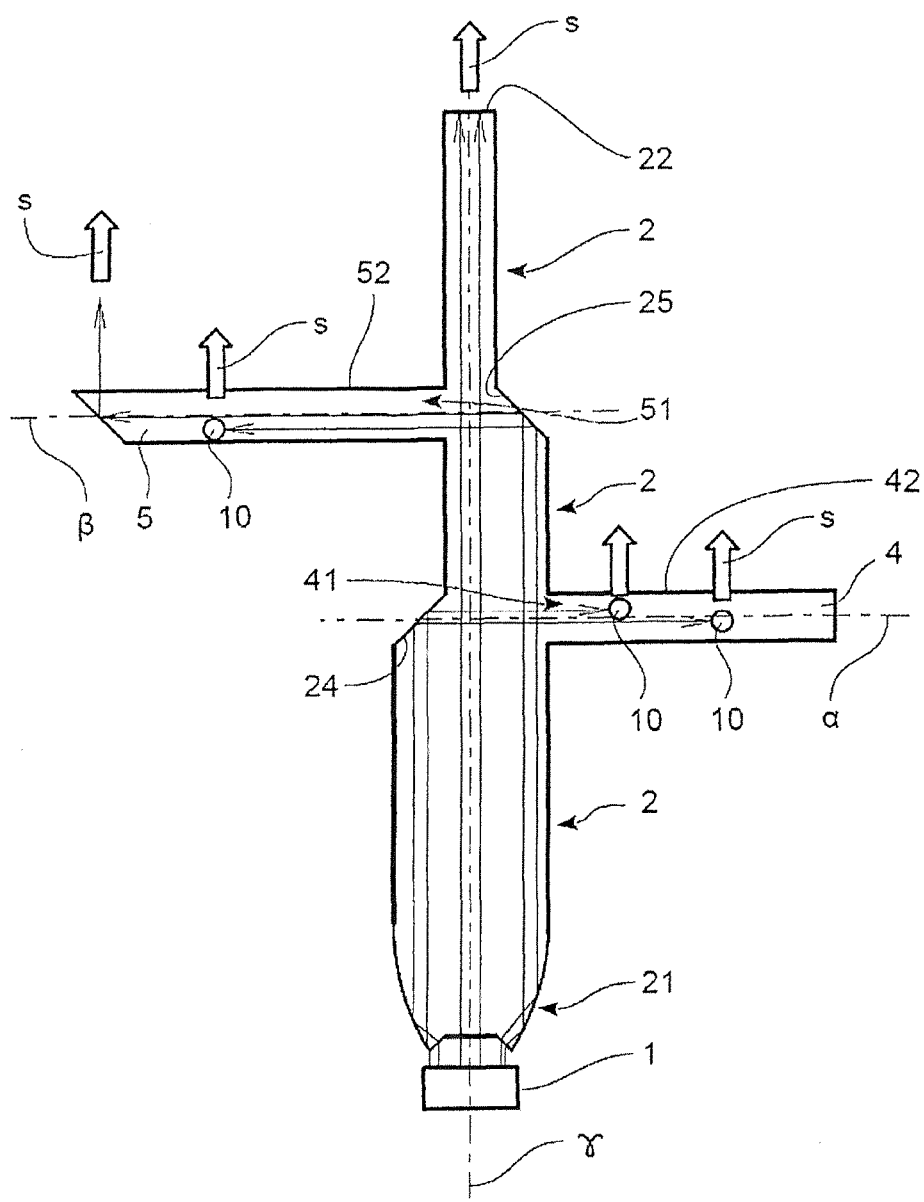

2012/0020103 A1* 1/2012 Okada ................ B60Q 1/2607
                                                        362/510
2014/0247617 A1    9/2014 De Lamberterie

FOREIGN PATENT DOCUMENTS

| DE | 102006016679 A1 | 10/2007 |
| DE | 102010045052 A1 | 3/2012 |
| DE | 102011000038 A1 | 7/2012 |
| DE | 102011002281 A1 | 10/2012 |
| EP | 2363738 A2 | 9/2011 |
| EP | 2548769 A1 | 1/2013 |
| JP | 2008166072 A | 7/2008 |

* cited by examiner

SIGNAL LAMP

FIELD OF THE INVENTION

The invention relates to a signal lamp, especially a signal lamp of a motor vehicle, comprising at least one light source arranged at the entry of a longitudinal light guide, which is oriented with its longitudinal axis in the direction of the light exit from the lamp, with at least a portion of the light from the light source passing into a transversal light guide, which is oriented with its longitudinal axis transversally to the longitudinal axis of the light guide and fitted on a part of its casing with an exit surface for light exit from the lamp.

BACKGROUND INFORMATION

Rear lamps of motor vehicles are subject to the requirement that the emitted light beams should form various patterns that produce a spatial effect both in the lit up state and in the off state. Fulfillment of variable requirements is achieved by using of a number of LED light sources where its own reflector is assigned to each LED source. However, a high number of LED sources is inconvenient because LED sources must be laboriously adjusted and therefore it is desirable to restrict the number of LED sources. A restricted number of LED light sources conversely limits production of light effects.

The document DE102011002281 describes a lamp for motor vehicles with a light source consisting of a LED source and a flat light guide assigned to it that is arranged transversally to the optical axis of the lamp. The light source is arranged at one flat side of the light guide in its central part against the entry surface through which the light beams enter the light guide. A fully reflective surface is arranged against the entry surface in the central part of the light guide, the reflective surface deflecting the light beams emitted from the light source in the transversal direction to the optical axis of the lamp towards the marginal part of the light guide. In the marginal area distant from the optical axis, the flat light guide has another fully reflective surface to deflect the unbound light beam back in the direction of the optical axis, of the lamp. For exit of the light beam in the direction of the optical axis on its other flat side in the marginal area distant from the optical axis, the light guide has a light unbinding surface to unbind the light beam in the direction of the optical axis of the lamp. Thus, the fully reflective surfaces of the flat light guide first reflect the light beam in the radial direction, transversally to the optical axis A, and then, in an offset way, from the optical axis back in the direction that is parallel to the optical axis. One light source is assigned to the light guide. The light emitted around the perimeter of the flat light guide in the direction of the optical axis of the lamp produces a light curve of a shape corresponding to the shape of the flat light guide. However, inside this light curve there is a dark space through which no light is emitted from the light guide. Thus, a single light curve can be produced by one light guide, and to produce another light curve another flat light guide arranged in parallel to the first light guide must be used. The light guides can only be combined in a limited way because other light guides can only be added in such a manner that their light curves lie concentrically inside the light curve of the previous light guide, or completely apart from each other. A lamp with more light curves would be too voluminous, heavy, costly and impractical.

The document DE102010045052 discloses a light device designed to create a supplementary side signal light, additionally to the main tail light or brake light of the motor vehicle. The light device comprises a light source with a flat light guide assigned to it, having a light entry surface for the introduction of the light. The opposite large sides of the flat light guide totally reflect the introduced light in such a way to make it move forward through the flat light guide to its end at the opposite side with regard to the entry surface. At the end of the light guide there is an exit surface to unbind light from the light guide. The entry introductory surface and the exit unbinding surface are each created at the thin sides of the light guide. The exit surface is inclined and partly reflects the light beam in the transversal direction to the large side of the light guide, and the remaining part of the light beam passes through the inclined exit surface in the direction of direct propagation of light from the light source. The light exit surface can be made of two parts, so that the first part of the exit surface is inclined obliquely to the direction of direct propagation of light from the light source, and the other part of the exit surface is perpendicular to the direction of direct propagation of light from the light source. The first partial beam reflects from the inclined first part of the exit surface, exits transversally to the direction of direct propagation of light from the light sources and provides the first light function, and the other partial beam passes through the other part of the exit surface and provides another light function. The direction of direct propagation of light from the light source is equal to the longitudinal axis of the motor vehicle. Thus, the light device can create two light beams that are transversally inclined with regard to each other. The first function may be the directional light indicator and the other function may be the tail light. In the direction of the longitudinal axis of the motor vehicle, the light beam only exits from the light device through the thin side of the flat light guide, the size of which is limited. The length of the light guide in the longitudinal direction of the motor vehicle increases the depth of the bushing of the light device. If the flat light guide is arranged perpendicularly to the longitudinal axis of the motor vehicle, the light beam emitted in the direction of the longitudinal axis of the motor vehicle is limited by the size of the reflective surface of the light guide. If the light guides are arranged linearly in the longitudinal axis direction, the total depth of the light device bushing increases.

The document DE19652159 discloses a signal lamp that comprises an L-shaped light guide and a light source the light of which enters the light guide through the front surface of one arm of the light guide and exits from the light guide through the peripheral surface of the other arm of the light guide. The other arm of the light guide is made of glass or plastic, especially PMMA, polymethyl methacrylate, or polycarbonate, and on the casing surface it is fitted with an area from which a part of the light passing through the light guide exits. The light guide can be arranged in the lamp casing or along the edge of the lamp bushing, either inside or outside the lamp bushing so as not to influence the main light beam exiting from the lamp. The light guide can run along the whole perimeter of the lamp and it can generally have a curved shape, e.g. circular. The light guide arms, arranged perpendicularly to each other, can be connected with a rounded transition piece. The entry part of the light guide can consist of two separated light guides, out of which the first light guide forms the first arm connected to the perpendicularly arranged second arm by means of a rounded transitional piece. The second light guide of a cylindrical shape runs in parallel with the first arm of the first light guide, and in the area of the rounded transition between the first and second arm the second light guide opens out into the exit surface fitted with optical elements and in the light exit direction covering the rounded transition between the first and second arm. The exit area of the second light guide is larger than the size of the cross-section of the second light guide. The first light guide can form a nearly closed flat pattern of a rectangular shape, the neighbouring sides of which are connected to each other with a transition of a broken shape. A disadvantage of the arrangement of the first light guide in accordance with the document DE19652159 is its flat arrangement, which only makes it possible to use the light guide around the perimeter of the main lamp. Another disadvantage is the fact that in the rounded transition and broken transition between the neighbouring, mutually perpendicularly arranged arms of the light guide, the intensity of the luminous flux passing from one arm to the next arm is reduced.

The goal of the invention is to provide a signal lamp, especially a rear lamp for motor vehicles that actively produces light patterns with a spatial effect in the lit up state and in the off state maintains a spatial impression, produces a clear light outline, requires a small number of LED light sources to fulfil its function, has compact dimensions, and can be produced easily and at low costs.

SUMMARY OF THE INVENTION

The disadvantages of the prior art are substantially eliminated and the goal of the invention is met by a signal lamp, especially a signal lamp of a motor vehicle, comprising at least one light source arranged at the entry of a longitudinal light guide. The longitudinal light guide is oriented with its longitudinal axis in the direction of light exit from the lamp and at least some of the light from the light source passes into a transversal light guide oriented with its longitudinal axis transversally to the longitudinal axis of the longitudinal light guide. The transversal light guide is fitted on a part of its casing with an exit surface for exit of light from the lamp. The longitudinal light guide is fitted with at least two reflective surfaces that do not overlap when viewed in the direction of the longitudinal axis of the longitudinal light guide, and are inclined towards the axis of the longitudinal light guide to reflect light beams to at least two transversal light guides arranged with their entries against the reflective surfaces and with their exit surfaces at a distance from each other in the direction of light exit from the lamp.

According to one of preferred embodiments, the transversal light guides having a flat shape at least partially overlap with their exit surfaces in the direction of light exit from the lamp.

According to another of preferred embodiments the transversal light guides and the longitudinal light guide are integral parts of one body made of plastic. The transversal light guides preferably contain diffusion particles for guiding the luminous flux through the exit surfaces of the casing in the direction of light exit from the lamp.

According to one of preferred embodiments, for exit of light beams from the longitudinal light guide in the direction of the longitudinal axis, the longitudinal light guide is, in a part of its transversal section, provided with an exit surface that does not overlap with the reflective surfaces in the direction of the longitudinal axis.

According to one of preferred embodiments, the cross-section of the longitudinal light guide has, viewed in the direction of light exit from the lamp, a closed circular or broken shape or the shape of a closed hollow or open profile.

The advantages of the signal lamp in accordance with the invention mainly reside in that it actively produces light patterns with a spatial effect in the lit up state and in the off state it maintains a spatial impression, creates a clear light outline of light patterns, creates light outlines of various intensities by the exit surfaces of the transversal light guides partly overlapping in the light exit direction, enables combination of light exiting directly from the longitudinal light guides and light outlines of variable intensities, is economical because it needs a low number of LED light sources to fulfill its function, and it is easy to produce at low costs by means of the pressure injection moulding process.

OVERVIEW OF FIGURES IN THE DRAWINGS

Figure 2:
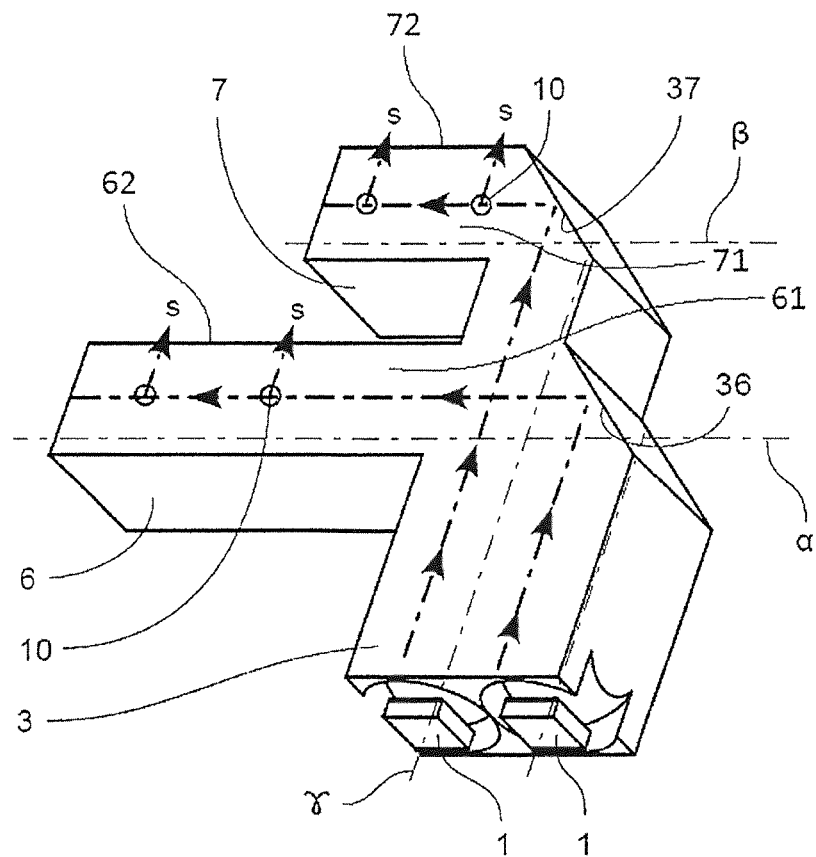
Figure 3:
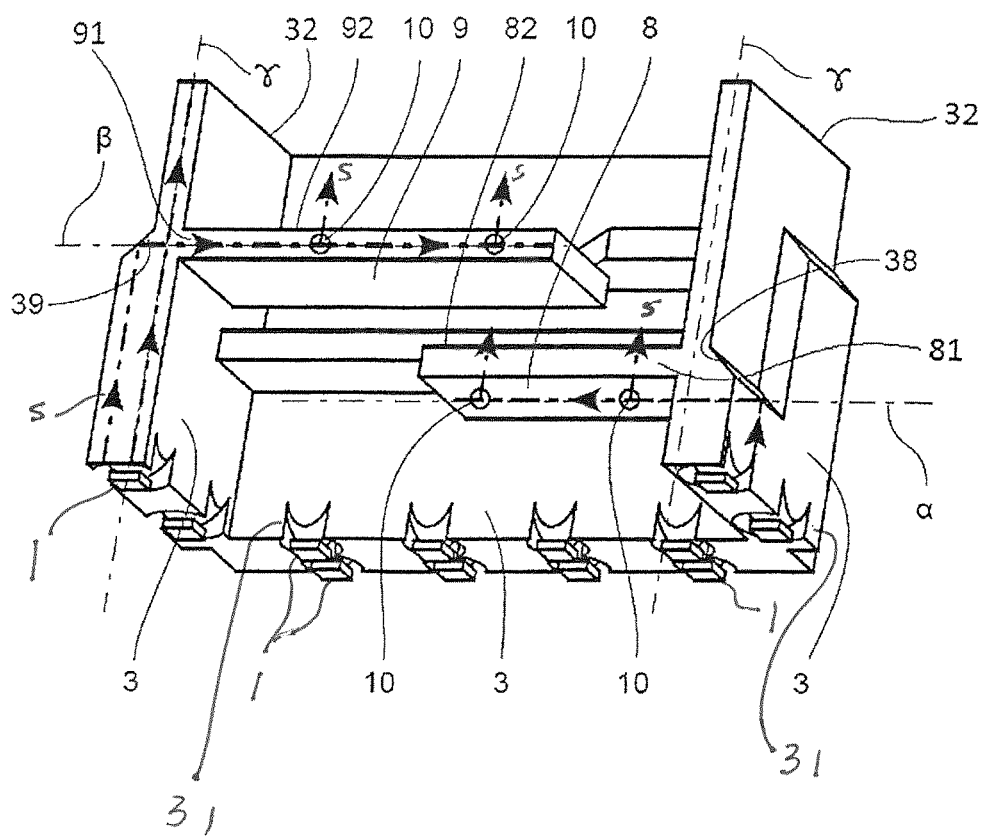

The signal lamp in accordance with the invention is clarified with the use of drawings where:

FIG. 1 shows the light guide of a signal lamp in a longitudinal cross-sectional view, FIG. 2 shows the light guide of a signal lamp in a perspective view, and FIG. 3 shows another embodiment of a light guide of the signal lamp in a perspective view.

EMBODIMENT EXAMPLES

With reference to FIG. 1, a light source 1 seated in the entry part 21 of the light guide 2 in its longitudinal axis γ is assigned to the light guide 2. The light guide 2 is arranged longitudinally in the direction s of light exit from the signal lamp. Transversal light guides 4, 5 with mutually opposite orientation are arranged transversally to the longitudinal axis γ of the light guide 2, while according to FIG. 1 they form a single part with the longitudinal light guide 2. The transversal light guides 4, 5 are preferably oriented with their longitudinal axes α, β perpendicularly to axis γ of the longitudinal light guide 2, and are arranged with their entries 41, 51 against the reflective surfaces 24, 25. Reflective surfaces 24, 25 are arranged in the light guide 2 at an inclination with regard to the longitudinal axis γ of the light guide 2, to reflect light beams to the respective transversal light guides 4, 5. Viewed in the direction of the longitudinal axis γ of the light guide 2, the reflective surfaces 24, 25 do not overlap. On a part of their casing, oriented in the direction s of light exit from the light guide, the transversal light guides 4, 5 are fitted with exit surfaces 42, 52 for exit of light from the lamp. For light exit from the transversal light guides 4, 5, their ends can be fitted with separate exit surfaces, made up e.g. of surfaces arranged obliquely with regard to axis β. The transversal light guides 4, 5 are arranged in the direction s of light exit from the lamp with their exit surfaces 42, 52 at a distance from each other. By way of an example, the transversal light guides 4, 5 are oriented in mutually opposite directions perpendicularly to axis γ of the longitudinal light guide 2, with their entries 41, 51 against the reflective surfaces 24, 25, which are inclined at the angle of 45° with respect to axis γ.

However, the transversal light guides 4, 5 can protrude from the longitudinal light guide 2 in the same direction with regard to axis γ, and in the light exit direction s they can partly and completely overlap as illustrated in the next figures.

The transversal light guides 4, 5 can protrude from the longitudinal light guide with their axes α, β inclined with respect to axis γ. In this case, the reflective surfaces 24, 25 must be inclined to axis γ at an angle that equals to half the inclination of axes α, β of the transversal light guides 4, 5 with respect to axis γ of the longitudinal light guide 2.

A part of the light beams emitted from the light source 1 directly follows the direction of the longitudinal axis γ of the light guide 2. The entry part 21 of the longitudinal light guide 2 has a concave shape of a reflector that reflects the other part of the light beams emitted from the light source 1 at an inclination to the longitudinal axis γ in the direction of the longitudinal axis γ. Thus, the cross-section of the light guide 2 has a larger area than the light-emitting surface of the light source 1. The transversal section, or cross-section of the longitudinal light source 2 can have, viewed in the direction s of light exit from the lamp, or in the direction of the longitudinal axis γ, respectively, a circular or broken shape. The projections of the reflective surfaces 24, in the direction of the longitudinal axis γ into the transversal section of the light guide 2 cover a part of the area of the transversal section of the light guide 2. Thus, the reflective surfaces 24, 25 only reflect a part of the light beams emitted from the light source 1 into the transversal light guides 4, 5, and their remaining part moves forward in the direction of the longitudinal axis γ of the light guide 1, which is equal to the direction s of light exit from the lamp. In the example shown in FIG. 1, the longitudinal light guide 2 for emission of light beams in the direction of the longitudinal axis γ is fitted with an exit surface 22 in a part of its cross-section that does not overlap with the reflective surfaces 24, 25 in the longitudinal axis direction γ. A part of the light beams from the light source 1 directly moves forward through the light guide in the direction of the longitudinal axis γ and exits through the exit surface 22 without reflection in the direction of light exit from the lamp. The light exiting directly through the exit surface 22 has a different intensity from that of the light exiting through the exit surfaces 42, 52 from the casing of the transversal light guides 4, 5. A part of the light beams from the light source 1 reflects on the reflective surfaces 24, 25 and the reflected light beams continue to the transversal light guides 4, 5, which contain diffusion particles 10 for dispersion and guiding of the luminous flux through the exit surfaces 42, 52 of the casing in the direction s of light exit from the transversal light guides, or the lamp, respectively. The transversal light guides 4, 5 are made as one piece with the light guide 2 by means of the process of pressure plastic injection moulding.

With reference to FIG. 2, the longitudinal light guide 3 is fitted with light sources 1 whose luminous flux enters the light guide 3 in the direction of the longitudinal axis γ. The light guide 3 is fitted with reflective surfaces 36, 37 inclined to the longitudinal axis γ to reflect light beams to the transversal light guides 6, 7, arranged with their entries 61, 71 against the reflective surfaces 36, 37. The projections of the reflective surfaces 36, 37 onto the plane perpendicular to the longitudinal axis γ do not overlap. A part of the light beams from the light sources 1 moves forward in the direction of the longitudinal axis γ, reflects from the reflective surface 36 and enters the transversal light guide 6 in the direction of its longitudinal axis α, and is dispersed by the diffusion particles 10 and exits through the exit surface 62 in the direction s of light exit from the lamp. The transversal light guides 6, 7 having a flat shape at least partially overlap with their exit surfaces 62, 72 in the direction s of light exit from the lamp. The light guide 6 exceeds the light guide 7, as viewed in the direction of the longitudinal axis γ. A part of the light beams from the light sources 1 moves forward in the direction of the longitudinal axis γ, reflects from the reflective surface 37 and enters the transversal light guide 7 oriented in the direction of the longitudinal axis β in the same direction as the transversal light guide 6, and is dispersed by the diffusion particles 10 and exits through the exit surface 72 in the direction s of light exit from the lamp. The transversal light guides 6, 7 partly overlap in the direction of the longitudinal axis γ. A part of the light beams exiting through the exit surface 62 directly exits from the lamp and a part passes through the transversal light guide 7 before it exits from the lamp. Either of the said parts of light beams has a different intensity. With a suitable colouring of the transversal light guide 7 the light beams exiting directly from the lamp and the light beams passing through the transversal light guide 7 first have different colours.

With reference to FIG. 3, the longitudinal light guide 3 in the transversal section, viewed in the direction s of light exit from the lamp, has the open shape of a U-profile. It includes plate-like walls on the first narrow sides of which the light sources 1 are arranged at entry parts 31, and on the other opposite narrow sides of which the plate-like walls have the exit surfaces 32. The flat sides of the plate-like walls are reinforced on the outer side of the U-profile of the longitudinal light guide 3 and the reinforcement is terminated with reflective surfaces 38, 39 to reflect the light beams passing through the walls of the light guide 3 to the transversally arranged transversal light guides 8, 9 protruding from the walls on the inner side of the U-profile of the light guide 3. Entries 81, 91 of transversal light guides 8, 9 are arranged against reflective surfaces 38, 39 respectively. The transversal light guides 8, 9 can also include diffusion particles 10 to disperse the light beans traveling therethrough. The transversal light guides 8, 9 with axes α, β protrude from the walls of the longitudinal light guides at a distance from each other in the direction s of light exit from the lamp, and in directions oriented against each other, with their ends mutually overlapping. Thus, viewed in the direction s of light exit from the lamp, the transversal light guides 8, 9 partly mutually overlap. The overlap of the transversal light guides 8, 9 causes a different intensity of the luminous flux exiting directly from the exit surface 92 of the light guide 9, and the luminous flux exiting from the exit surface 82 of the transversal light guide 8 and passing through the light guide 9 before it exits from the lamp. Colour differentiation of the said luminous fluxes can also be selected and arranged. The transversal light guides 8, 9 can also include diffusion particles 10 to disperse the light beans traveling therethrough.

The shape of the longitudinal light guide 2, 3 can also be different than shown in the drawing figures. In the transversal section, or cross-section, respectively the longitudinal light guide 2, 3 can have, viewed in the direction s of light exit from the lamp, a closed shape of a circle or broken closed flat formation, or it can e.g. have the shape of a profile whose walls create a closed pattern of an annular formation, a thick-walled rectangle, or a closed pattern of a corner profile.

LIST OF REFERENCE MARKS 1 light source
2, 3 longitudinal light guide
4,5,6 transversal light guide
7,8,9 light guide
10 diffusion particles
21 entry part
22 exit surface
24 reflective surface
25 reflective surface
31 entry part
32 exit surface
36 reflective surface
37 reflective surface
38 reflective surface 39 reflective surface
41 entry
42 exit surface
51 entry
52 exit surface
61 entry
62 exit surface
71 entry
72 exit surface
81 entry
82 exit surface
91 entry
92 exit surface
α longitudinal axis (of a transversal light guide)
β longitudinal axis (of a transversal light guide)
γ longitudinal axis (of the longitudinal light guide)
s direction of light exit from the lamp

The invention claimed is:

1. A signal lamp for a motor vehicle, the signal lamp comprising at least one light source (1) arranged at the entry of a longitudinal light guide (2, 3), wherein the longitudinal light guide is oriented with its longitudinal axis (γ) in the direction (s) of light exit from the lamp and passes into a transversal light guide (4, 5, 6, 7, 8, 9) oriented with its longitudinal axis (α, β) transversally to the longitudinal axis (γ) of the longitudinal light guide (2, 3) and fitted on a part of its casing with an exit surface (42, 52, 62, 72, 82, 92) for exit of light from the lamp, and further wherein the longitudinal light guide (2, 3) is fitted with at least two reflective surfaces (24, 25, 36, 37, 38, 39) that do not overlap when viewed in the direction of the longitudinal axis (γ) of the longitudinal light guide (2, 3), and are inclined towards the axis (γ) of the longitudinal light guide (2, 3) to reflect light beams to at least two transversal light guides (4, 5, 6, 7, 8, 9) which are arranged with their entries (41, 51, 61, 71, 81, 91) against the reflective surfaces (24, 25, 36, 37, 38, 39) and with their exit surfaces (42, 52, 62, 72, 82, 92) at a distance from each other in the direction (s) of light exit from the lamp, wherein the transversal light guides (6, 7) having at least a partial flat shape at least partially overlap with their exit surfaces (62, 72) in the direction (s) of light exit from the lamp.

2. The signal lamp according to claim 1, wherein the transversal light guides (4, 5, 6, 7, 8, 9) and the longitudinal light guide (2, 3) are integral parts of one body made of plastic.

3. The signal lamp according to claim 2, wherein the transversal light guides (4, 5, 6, 7, 8, 9) contain diffusion particles (10) for guiding the luminous flux through the exit surfaces (42, 52, 62, 72, 82, 92) of the casing in the direction (s) of light exit from the lamp.

4. The signal lamp according to claim 1, wherein for exit of light beams from the longitudinal light guide (2, 3) in the direction of the longitudinal axis (γ), the longitudinal light guide (2, 3) is, in a part of its transversal section, provided with an exit surface (22, 32) that does not overlap with the reflective surfaces (24, 25, 26, 27, 28, 29) in the direction of the longitudinal axis (γ).

5. The signal lamp according to claim 1, wherein the cross-section of the longitudinal light guide (2, 3) has, viewed in the direction (s) of light exit from the lamp, a closed circular or broken shape or the shape of a closed hollow or open profile.

* * * * *